(12) United States Patent
Greenberg et al.

(10) Patent No.: US 8,457,752 B2
(45) Date of Patent: Jun. 4, 2013

(54) NEURAL STIMULATION FOR INCREASED CONTRAST

(75) Inventors: Robert J. Greenberg, Los Angeles, CA (US); Matthew J. McMahon, Los Angeles, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 791 days.

(21) Appl. No.: 11/521,681

(22) Filed: Sep. 15, 2006

(65) Prior Publication Data

US 2007/0073358 A1    Mar. 29, 2007

Related U.S. Application Data

(60) Provisional application No. 60/718,093, filed on Sep. 16, 2005.

(51) Int. Cl.
*A61N 1/00*           (2006.01)

(52) U.S. Cl.
USPC ............................... 607/54; 607/53; 600/383

(58) Field of Classification Search
USPC ..................................... 600/558; 607/53, 54
See application file for complete search history.

(56) References Cited

U.S. PATENT DOCUMENTS

| | | |
|---|---|---|
| 5,109,844 A | 5/1992 | de Juan, Jr. et al. |
| 5,935,155 A | 8/1999 | Humayun et al. |
| 5,944,747 A | 8/1999 | Greenberg et al. |
| 6,400,989 B1 | 6/2002 | Eckmiller |
| 6,458,157 B1 | 10/2002 | Suaning |
| 6,507,758 B1 | 1/2003 | Greenberg et al. |
| 6,530,954 B1 | 3/2003 | Eckmiller |

(Continued)

FOREIGN PATENT DOCUMENTS

WO    WO 00/56244    9/2000

OTHER PUBLICATIONS

Tehovnik, Edward J. et al. "Microstimulation of V1 affects the detection of visual targets: manipulation of target contrast." Exp Brain Res 165 Jun. 2005: 305-314.*

(Continued)

*Primary Examiner* — Allen Porter, Jr.
(74) *Attorney, Agent, or Firm* — Scott B. Dunbar; Alessandro Steinfl

(57) ABSTRACT

The present invention is a method of improving the contrast of electrical neural stimulation and expanding the dynamic range for brightness, and specifically a method of improving the contrast of an image supplied to the retina, or visual cortex, through a visual prosthesis. The background brightness for a blind subject is often not perfectly black, but a dark gray or brown. When stimulating visual neurons in the retina, low current stimulation tends to create a dark percept, the perception of a phosphene darker than the background brightness level perceived in the un-stimulated state. The human retina contains neurons that signal light increments ("on" cells) and neurons that signal light decrements ("off" cells). In a healthy retina, the on cells tend to fire in response to an increase in light above the background level, while the off cells tend to fire in response to a decrease in light below the background level.

13 Claims, 4 Drawing Sheets

U.S. PATENT DOCUMENTS

| | | | |
|---|---|---|---|
| 6,611,716 B2 * | 8/2003 | Chow et al. | 607/54 |
| 6,920,358 B2 | 7/2005 | Greenberg et al. | |
| 2002/0091421 A1 | 7/2002 | Greenberg et al. | |
| 2004/0078064 A1 * | 4/2004 | Suzuki | 607/54 |
| 2004/0176821 A1 | 9/2004 | Delbeke et al. | |
| 2005/0090875 A1 * | 4/2005 | Palanker et al. | 607/54 |
| 2005/0273141 A1 | 12/2005 | Greenberg et al. | |
| 2006/0167528 A1 | 7/2006 | Roy et al. | |
| 2006/0184062 A1 | 8/2006 | Greenberg et al. | |
| 2006/0190058 A1 | 8/2006 | Greenberg et al. | |

OTHER PUBLICATIONS

Cottaris, Nicolas et al. "How the retinal network reacts to epiretinal stimulation to form the prosthetic visual input to the cortex." J. Nneural Eng. 2 (2005) S74-S90.*

Margalit, M.D., PhD, Eyal, et al; Retinal Prosthesis for the Blind; Survey of Ophthalmology; vol. 47; No. 4, Jul.-Aug. 2002; by Elsevier Science; pp. 335-356.

Margalit, M.D., PhD, Eyal, et al.; Artificial Vision Devices; Clinical & Refractive Optometry7, 15:7/8, 2004; pp. 216-221.

* cited by examiner

NEURAL STIMULATION FOR INCREASED CONTRAST

CROSS REFERENCE TO RELATED APPLICATIONS

This application claims the benefit of U.S. Provisional Application No. 60/718,093, "Visual Neural Stimulation Method for Increased Contrast", filed Sep. 16, 2005, the disclosure of which is incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of neural stimulation for improved contrast and dynamic range for brightness.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across retinal neuronal cell membranes, which can initiate retinal neuronal action potentials, which are the means of information transfer ih the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the retinal neurons, and avoid undue compression of the retinal neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

It is known that neurons respond best to change in stimuli. The retina, if continuously stimulated in a consistent manner, will slowly become less and less sensitive to the stimulus. This causes the perception of a constant visual image to gradually disappear. Those with normal vision are unable to perceive this effect because the eye constantly moves, motions called jitter or microsaccades. A normal retina has a resolution of approximately four million light transducer cells (rods and cones), hence it requires a minute movement to change the light intensity cast upon a given light transducer.

A retinal prosthesis, according to the present invention, has two disadvantages. First, the resolution of an electrode array applied to the retina is significantly lower than the resolution of a healthy retina, requiring a greater movement to move an image from one electrode to the next electrode, as compared to one cone to the next cone. Further, a head mounted camera does not have the natural jitter or microsaccades of an eye. Therefore it is necessary to achieve the required change in another manner.

It is also known that some neural processing is done within the retina. Hence, a continuously stimulated cone will not result in a continuous signal to the brain. Ganglion and bipolar cells pass along this change in information more readily than constant information. In a diseased retina, rods and cone cannot be stimulated, since they are dead. Electrically stimulating cells further along the neural pathway, bypasses some of the neural processing. This processing must be simulated electronically to gain normal brain stimulation.

The ability to perceive a constant image or image contrast is necessary to the design of a visual prosthesis.

SUMMARY OF THE INVENTION

The present invention is a method of improving the contrast of electrical neural stimulation and expanding the dynamic range for brightness, and specifically a method of improving the contrast of an image supplied to the retina, or visual cortex, through a visual prosthesis. The background brightness for a blind subject is often not perfectly black, but a dark gray or brown.

When stimulating visual neurons in the retina, low current stimulation tends to create a dark percept, the perception of a phosphene darker than the background brightness level perceived in the un-stimulated state. The human retina contains neurons that signal light increments ("on" cells) and neurons that signal light decrements ("off" cells). In a healthy retina, the on cells tend to fire in response to an increase in light above the background level, while the off cells tend to fire in response to a decrease in light below the background level.

Currently available electrodes for neural stimulation are much larger than individual neural cells and stimulate multiple cells at once, including the simultaneous stimulation of on and off cells. It appears, on the basis of in vitro physiological recordings, that the off cells have a lower threshold for stimulation. That is, off cells may be stimulated by an electrical current too low to stimulate on cells. Thus, neurons that signal light decrements to the brain may be stimulated by low current levels that do not stimulate the spatially coextensive on cells. This selective stimulation of the off pathway for vision yields a "dark" phosphene. As current increases and on cells begin to respond in addition to off cells, the on cells overwhelm the off cells giving the perception of a light phosphene. During the transition from darkening to brightening, there may be a bright phosphene within a dark surround. This is cause by more on cells being stimulated near the center of the electrode and more off cells being stimulated at a slight distance from the center of the electrode where the neurons receive less current.

Individual cells have a slightly different threshold and a slightly different distance from the electrode. Hence, gradually increasing current will cause greater and greater numbers of cells to fire.

At low current, a few off cells are stimulated causing a slight darkening of the phosphene. As current increases, more off cells are stimulated causing more darkening of the phosphene. Further current increase causes a few on cells to be stimulated causing the phosphene to lighten again. As current increases, more on cells are stimulated causing a gradual brightening of the phosphene.

It should be noted that both lightening and darkening functions are generally exponential with transitions where on cells begin to overcome off cells, at nominal threshold and approaching saturation of the on cells.

It is therefore advantageous to create a map of responses to current utilizing the darkening effect to create a greater dynamic range in response to neural stimulation. The map will vary from patient to patient and from electrode to electrode, although geographically close electrodes will probably elicit a similar response.

It is necessary to create a software table of response maps within a video processing unit, which modifies the linear input brightness information for each pixel in the input video image to conform to the response map for each electrode.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
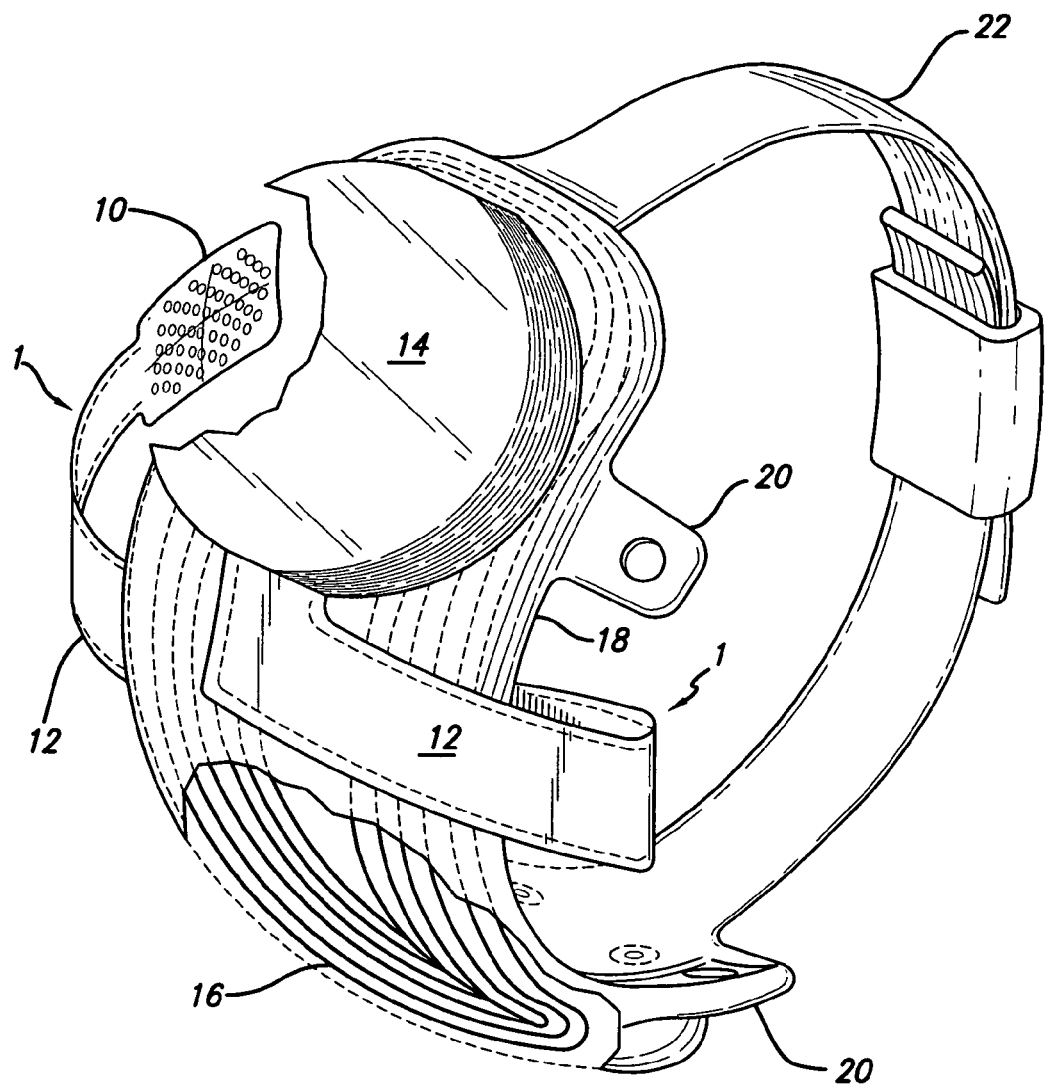
FIG. 1 is a perspective view of the implanted portion of the preferred retinal prosthesis.

FIG. 1 shows a perspective view of the implanted portion of the preferred retinal prosthesis. An electrode array 10 is mounted by a retinal tack or similar means to the epiretinal surface. The electrode array 10 is electrically coupled by a cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil may be made from a thin film polymer sandwich with wire traces deposited between layers of thin film polymer. The electronics package 14 and secondary inductive coil 16 are held together by a molded body 18. The molded body 18 may also include suture tabs 20. The molded body narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. It is an advantage of the present design, that the entire implanted portion of the prosthesis is attached to and supported by the sclera. By placing the device under the rectus muscles with the electronics package in an area of fatty issue between the rectus muscles, eye motion does not cause any flexing which might fatigue, and eventually damage, the device.

Figure 2:
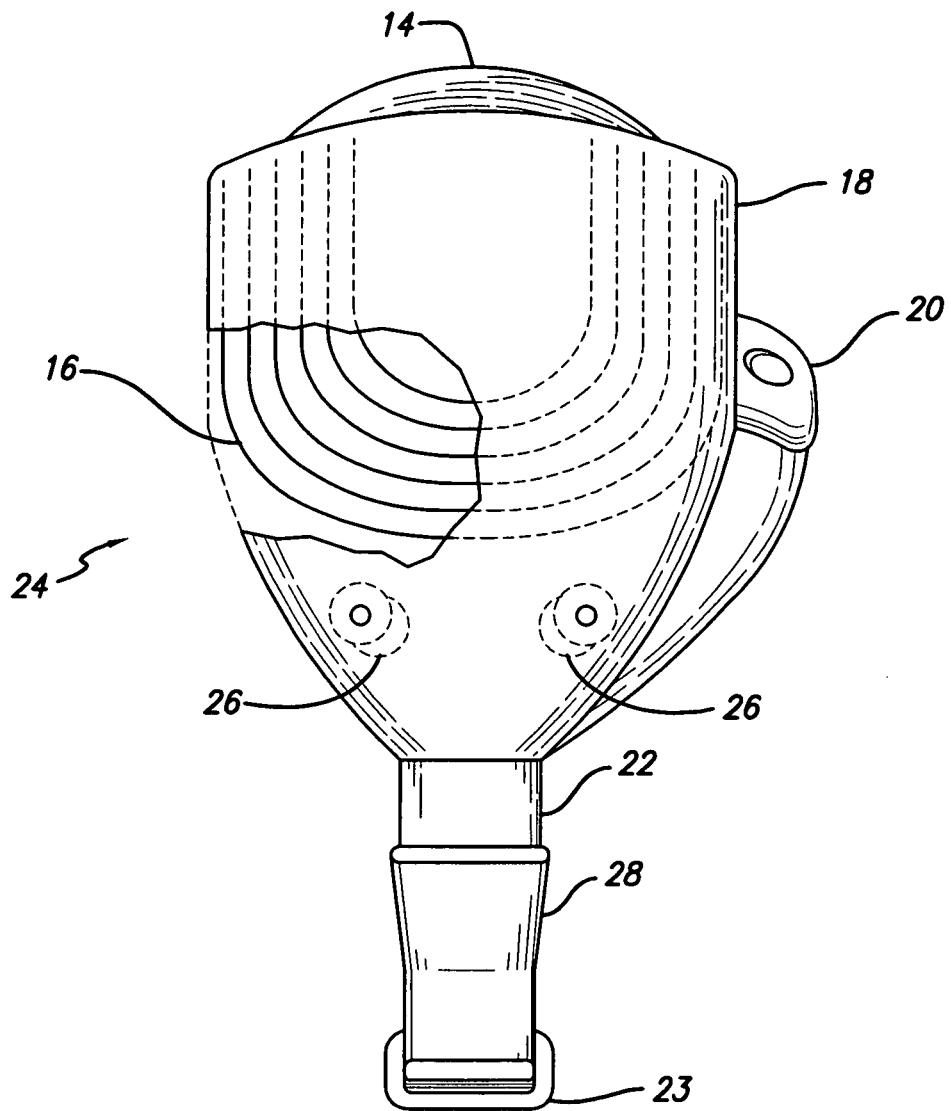
FIG. 2 is a side view of the implanted portion of the preferred retinal prosthesis showing the fan tail in more detail.

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body is shaped in the form of a fan tail 24 on the end opposite the electronics package 14.

Figure 3:
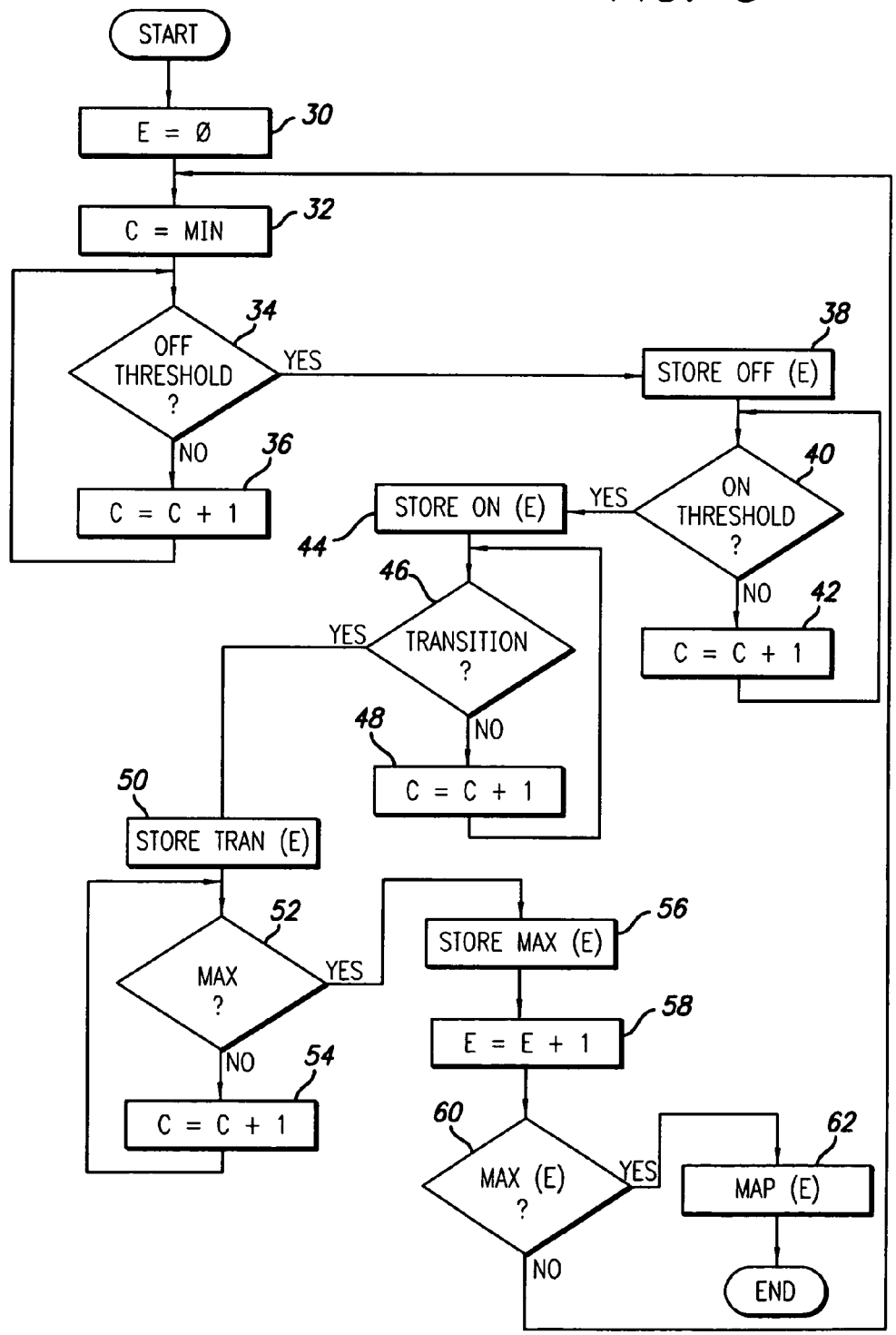
FIG. 3 depicts a flow chart showing the processing in the preferred embodiment.

FIG. 3 is a flow chart showing the basic operation of the brightness mapping procedure. The process begins by setting the electrode counter E to zero 30, and the current level C to a preset minimum 32. The off threshold is tested 34. If the off threshold has not been reached, the current is increased 36 and the process is repeated. Once the off threshold is reached it is stored in a data array at off(E), the off threshold for electrode E 38. Then the on threshold is tested 40. If the on threshold ha not been reached, current is increased 42 and the process is repeated. Once the on threshold is reached, it is stored in the data array as on(E) 44. Then the transition from dark to light is tested 46. If the transition has not been reached, current is increased 48 and the process repeated. Once the transition has been reached, it is stored in the data array as trans(E) 50. Next, the maximum stimulation level is tested 52. If the maximum stimulation level has not been reached, the current is increased 54 and the process repeated. Once, the maximum stimulation level has been reached it is stored in the data array as max(E) 56. Then, E, the electrode counter, is incremented 58. Next, the electrode counter E is compared with a maximum number of electrodes 60. If the maximum number of electrodes has not been reached, the process returns to step 32. If the maximum number of electrodes has been reached, the mapping process begins.

The video data provides a discrete number of brightness levels. Those brightness levels are mapped first inversely to current levels between off(E) and on(E), and then proportionately from trans(E) to max(E). Note that currently levels between on(E) and trans(E) are not used, as those brightness level can be obtained with lower currents between off(E) and on(E). It should also be noted that the mapping is not linear as the relationship between current to brightness between off(E) and on(E) is inverse and exponential. While the relationship of current to brightness between trans(E) and max(E) is not inverse and logarithmic.

Figure 4:
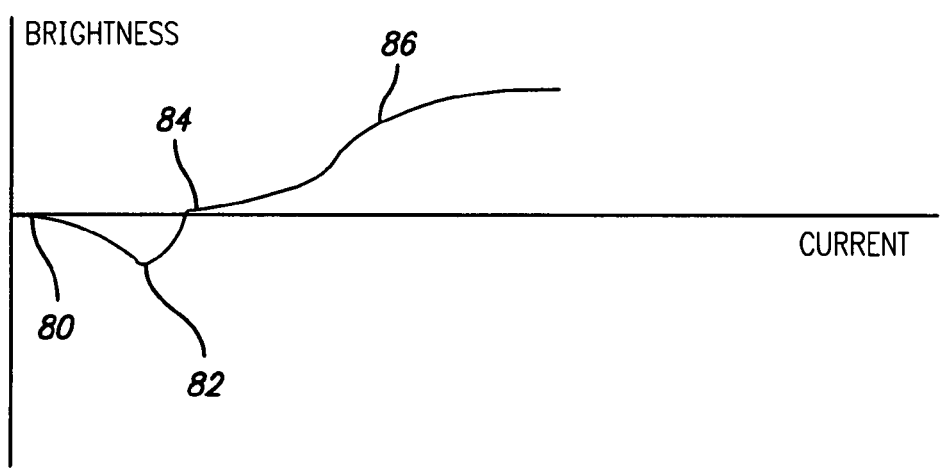
FIG. 4 depicts a typical perceptual pattern for a single electrode.

FIG. 4 is a graph with brightness on the vertical axis and current on the horizontal axis. As current is increase from zero there is first no reaction. When the off cell threshold 80 is reached, the patient perceives a dark spot. As current further increases, the spot grows darker. Note that the darkening response in exponential. At the on cell threshold 82, the spot grows lighter. As current increases further there is a transition point 84 where the on cells overwhelm the off cells and the spot begins to grown lighter than the point of no stimulation. The relationship of current to brightness becomes logarithmic 86 with decreasing marginal brightness in response to increasing current.

It should be noted that each electrode will elicit a different response to each stimulation level. The most accurate map is obtained by testing and storing data from each electrode. As the number of electrodes increase this becomes more and more difficult. However, cell which are geographically related, that is near each other on the retina or visual cortex, tend to have similar response characteristics. Hence, if it is prohibitive to map electrode individually, the electrode can be mapped as small groups of adjacent electrodes.

Accordingly, what has been shown is an improved method of making a neural prosthesis and improved method of stimulating neural tissue. While the invention has been described by means of specific embodiments and applications thereof, it is understood that numerous modifications and variations could be made thereto by those skilled in the art without departing from the spirit and scope of the invention. In particular, the preferred embodiment describes a retinal prosthesis for artificial vision. It should be obvious to one skilled in the art that the invention has broad applicability to other types of neural stimulation. It is therefore to be understood that within the scope of the claims, the invention may be practiced otherwise than as specifically described herein.

The invention claimed is:

1. A method of visual neural stimulation comprising:

applying a stimulation current to retinal cells of a patient with an electrode array that is electrically connected with a retinal prosthesis;

determining an off cell threshold of the retinal cells by increasing the stimulation current from zero until a spot is perceived by the patient such that, by further increasing the stimulation current, the spot grows darker;

determining an on cell threshold of the retinal cells by further increasing the stimulation current such that, at the on cell threshold, the spot grows lighter;

determining a transition point of the retinal cells where on cells overwhelm off cells;

developing a stimulation map based on said off cell threshold, said on cell threshold and said transition point; and stimulating the retinal cells with said electrode array according to said stimulation map to create a perception of light for the patient and to increase contrast between background and foreground phosphenes, where stimulation current between said off cell threshold and said transition point is used to darken a point in an image perceived by the patient.

2. The method according to claim 1, wherein the steps of claim 1 are repeated for each electrode of the electrode array, thus determining a plurality of different on cell thresholds and off cell thresholds for each electrode of the electrode array.

3. The method according to claim 1, wherein the steps of claim 1 are repeated for multiple groups of electrodes of the electrode array, thus determining a plurality of different on cell thresholds and off cell thresholds for each group of electrodes of the electrode array.

4. The method according to claim 3, wherein said multiple groups of electrodes are geographically determined.

5. The method according to claim 1, further comprising determining a maximum stimulation level of the retinal cells and where said stimulation map is based on said off cell threshold, said transition point and said maximum stimulation level.

6. The method according to claim 5, wherein the stimulation map defines a logarithmic and non-inverse relationship between the transition point and the maximum stimulation level.

7. The method according to claim 1, wherein a brightness level perceived by the patient between said off cell threshold and said transition point is lower than a brightness level perceived by the patient in an un-stimulated state.

8. The method according to claim 1, wherein at the transition point the spot begins to grow lighter than a point of no stimulation.

9. The method according to claim 1, wherein stimulating retinal cells according to said stimulation map comprises
providing in the electrode array, individual electrodes larger than individual retinal cells, and
stimulating on cells and off cells of the patient simultaneously with each of the individual electrodes.

10. The method according to claim 1, wherein stimulating retinal cells according to said stimulation map includes simultaneous stimulation of on cells and off cells.

11. The method according to claim 1, wherein when determining an off cell threshold, off cells are stimulated by a stimulation current too low to stimulate on cells.

12. The method according to claim 11, wherein, as the stimulation current increases, on cells begin to respond in addition to off cells.

13. The method according to claim 1, wherein the stimulation map defines an inverse and exponential relationship between said off cell threshold and said on cell threshold.

* * * * *